US006770247B1

(12) United States Patent
Romack et al.

(10) Patent No.: US 6,770,247 B1
(45) Date of Patent: Aug. 3, 2004

(54) LIQUID PRODUCT VAPORIZING APPARATUS FOR AN AIR DEODORIZING SYSTEM

(75) Inventors: Keith D. Romack, Newton, IL (US); Ricke D. Shamhart, Newton, IL (US)

(73) Assignee: Triad Industries, Inc., Newton, IL (US)

( * ) Notice: Subject to any disclaimer, the term of this patent is extended or adjusted under 35 U.S.C. 154(b) by 166 days.

(21) Appl. No.: 09/625,603

(22) Filed: Jul. 26, 2000

Related U.S. Application Data

(63) Continuation-in-part of application No. 09/224,647, filed on Dec. 31, 1998, now abandoned.
(60) Provisional application No. 60/070,357, filed on Jan. 2, 1998.

(51) Int. Cl.[7] ............................ A62B 7/08; A61L 9/00; B01D 47/06; B01D 39/00

(52) U.S. Cl. ............................ 422/123; 422/4; 422/5; 422/124; 422/168; 422/172; 422/306; 261/78.2; 261/115; 96/222; 96/227

(58) Field of Search ......................... 422/4–5, 123–124, 422/168, 306, 172; 261/78.2, 115; 96/222, 227

(56) References Cited

U.S. PATENT DOCUMENTS 3,594,980 A * 7/1971 Diehl
3,969,479 A 7/1976 Lonnes et al. .............. 423/210
4,067,692 A 1/1978 Farris .......................... 21/74 R
4,238,461 A * 12/1980 Devries
4,256,710 A 3/1981 Azuma et al. .............. 423/210
4,844,874 A * 7/1989 deVries
5,030,253 A * 7/1991 Tokuhiro et al.
5,071,622 A 12/1991 Dunson, Jr. .................... 422/5
5,160,707 A 11/1992 Murray et al. .............. 422/170
5,248,448 A 9/1993 Waldron et al. ............ 252/305
5,302,359 A 4/1994 Nowatzki ................... 422/306
5,314,619 A 5/1994 Runyon ...................... 210/606
5,364,030 A 11/1994 Murdock et al. ........... 239/310
5,417,920 A 5/1995 Yung ............................. 422/5
5,549,247 A 8/1996 Rossman et al. ............. 239/57
5,567,402 A 10/1996 Vicard et al. ............ 423/245.2
5,766,547 A 6/1998 Kay et al. ...................... 422/5
5,989,497 A * 11/1999 Labonte, Jr.

OTHER PUBLICATIONS

Hinsilblon Laboratories EVANE/SCENT brochure, Apr. 23, 1997.

* cited by examiner

*Primary Examiner*—Robert J. Warden, Sr.
*Assistant Examiner*—Monzer R. Chorbaji
(74) *Attorney, Agent, or Firm*—Ice Miller; Jay G. Taylor

(57) ABSTRACT

A liquid product vaporizing apparatus for an air deodorizing system includes an air inlet port for drawing a stream of air into the system and directing the stream of air into a vaporization chamber. An atomizing nozzle sprays a mist of liquid deodorant from a liquid reservoir into the vaporization chamber as the stream of air flows through the vaporization chamber. Much of the atomized liquid deodorant vaporizes within the vaporization chamber. The vaporized particles of liquid deodorant mix with the stream of air flowing through the vaporization chamber to form a stream of treated air. Other particles of liquid deodorant condense and coalesce on the sidewall of the vaporization chamber and are drawn by gravity toward the liquid product reservoir so they may be re-sprayed from the atomizing nozzle. The treated air exits the vaporization chamber and is directed through distribution pipes to a plurality of vapor distribution ports. The treated air flows out of the vapor distribution ports and mixes with a malodor produced from industrial or other activity, such as a waste-water treatment plant. Mixing of the treated air with the malodor effectively neutralizes the malodor and makes the malodorous activity more tolerable to human life.

18 Claims, 13 Drawing Sheets

Maximum Vapor Caculation
Gallons Per hour

Blower CFM 1000
Coff 4.00

| | Temp F | | | | | | | | | | | | |
|---|---|---|---|---|---|---|---|---|---|---|---|---|---|
| **Humidity** | 40 | 45 | 50 | 55 | 60 | 65 | 70 | 75 | 80 | 85 | 90 | 95 | 100 |
| 40% | 0.788 | 0.945 | 1.130 | 1.344 | 1.594 | 1.882 | 2.214 | 2.596 | 3.033 | 3.531 | 4.099 | 4.742 | 5.470 |
| 45% | 0.722 | 0.867 | 1.036 | 1.232 | 1.461 | 1.725 | 2.030 | 2.379 | 2.780 | 3.237 | 3.757 | 4.347 | 5.014 |
| 50% | 0.657 | 0.788 | 0.941 | 1.120 | 1.328 | 1.568 | 1.845 | 2.163 | 2.527 | 2.943 | 3.416 | 3.952 | 4.558 |
| 55% | 0.591 | 0.709 | 0.847 | 1.008 | 1.195 | 1.411 | 1.661 | 1.947 | 2.275 | 2.649 | 3.074 | 3.557 | 4.103 |
| 60% | 0.525 | 0.630 | 0.753 | 0.896 | 1.062 | 1.255 | 1.476 | 1.731 | 2.022 | 2.354 | 2.732 | 3.161 | 3.647 |
| 65% | 0.460 | 0.551 | 0.659 | 0.784 | 0.930 | 1.098 | 1.292 | 1.514 | 1.769 | 2.060 | 2.391 | 2.766 | 3.191 |
| 70% | 0.394 | 0.473 | 0.565 | 0.672 | 0.797 | 0.941 | 1.107 | 1.298 | 1.516 | 1.766 | 2.049 | 2.371 | 2.735 |
| 75% | 0.328 | 0.394 | 0.471 | 0.560 | 0.664 | 0.784 | 0.923 | 1.082 | 1.264 | 1.471 | 1.708 | 1.976 | 2.279 |
| 80% | 0.263 | 0.315 | 0.377 | 0.448 | 0.531 | 0.627 | 0.738 | 0.865 | 1.011 | 1.177 | 1.366 | 1.581 | 1.823 |
| 85% | 0.197 | 0.236 | 0.282 | 0.336 | 0.398 | 0.470 | 0.554 | 0.649 | 0.758 | 0.883 | 1.025 | 1.186 | 1.368 |
| 90% | 0.131 | 0.158 | 0.188 | 0.224 | 0.266 | 0.314 | 0.369 | 0.433 | 0.505 | 0.589 | 0.683 | 0.790 | 0.912 |
| 95% | 0.066 | 0.079 | 0.094 | 0.112 | 0.133 | 0.157 | 0.185 | 0.216 | 0.253 | 0.294 | 0.342 | 0.395 | 0.456 |

Blower CFM 829
Coff 4.00

Maximum Vapor Caculation
Gallons Per hour

| Humidity | Temp F | | | | | | | | | | | | |
|---|---|---|---|---|---|---|---|---|---|---|---|---|---|
| | 40 | 45 | 50 | 55 | 60 | 65 | 70 | 75 | 80 | 85 | 90 | 95 | 100 |
| 40% | 0.653 | 0.784 | 0.937 | 1.115 | 1.321 | 1.560 | 1.836 | 2.152 | 2.514 | 2.928 | 3.398 | 3.931 | 4.535 |
| 45% | 0.599 | 0.718 | 0.858 | 1.022 | 1.211 | 1.430 | 1.683 | 1.973 | 2.305 | 2.684 | 3.115 | 3.604 | 4.157 |
| 50% | 0.544 | 0.653 | 0.780 | 0.929 | 1.101 | 1.300 | 1.530 | 1.793 | 2.095 | 2.440 | 2.832 | 3.276 | 3.779 |
| 55% | 0.490 | 0.588 | 0.702 | 0.836 | 0.991 | 1.170 | 1.377 | 1.614 | 1.886 | 2.196 | 2.548 | 2.948 | 3.401 |
| 60% | 0.435 | 0.522 | 0.624 | 0.743 | 0.881 | 1.040 | 1.224 | 1.435 | 1.676 | 1.952 | 2.265 | 2.621 | 3.023 |
| 65% | 0.381 | 0.457 | 0.546 | 0.650 | 0.771 | 0.910 | 1.071 | 1.255 | 1.467 | 1.708 | 1.982 | 2.293 | 2.645 |
| 70% | 0.327 | 0.392 | 0.468 | 0.557 | 0.661 | 0.780 | 0.918 | 1.076 | 1.257 | 1.464 | 1.699 | 1.966 | 2.267 |
| 75% | 0.272 | 0.327 | 0.390 | 0.464 | 0.550 | 0.650 | 0.765 | 0.897 | 1.048 | 1.220 | 1.416 | 1.638 | 1.889 |
| 80% | 0.218 | 0.261 | 0.312 | 0.372 | 0.440 | 0.520 | 0.612 | 0.717 | 0.838 | 0.976 | 1.133 | 1.310 | 1.512 |
| 85% | 0.163 | 0.196 | 0.234 | 0.279 | 0.330 | 0.390 | 0.459 | 0.538 | 0.629 | 0.732 | 0.849 | 0.983 | 1.134 |
| 90% | 0.109 | 0.131 | 0.156 | 0.186 | 0.220 | 0.260 | 0.306 | 0.359 | 0.419 | 0.488 | 0.566 | 0.655 | 0.756 |
| 95% | 0.054 | 0.065 | 0.078 | 0.093 | 0.110 | 0.130 | 0.153 | 0.179 | 0.210 | 0.244 | 0.283 | 0.328 | 0.378 |

FIGURE 11

Maximum Vapor Caculation
Gallons Per hour

Blower CFM 69
Coff 4.00

| | Temp F | | | | | | | | | | | | |
|---|---|---|---|---|---|---|---|---|---|---|---|---|---|
| Humidity | 40 | 45 | 50 | 55 | 60 | 65 | 70 | 75 | 80 | 85 | 90 | 95 | 100 |
| 40% | 0.054 | 0.065 | 0.078 | 0.093 | 0.110 | 0.130 | 0.153 | 0.179 | 0.209 | 0.244 | 0.283 | 0.327 | 0.377 |
| 45% | 0.050 | 0.060 | 0.071 | 0.085 | 0.101 | 0.119 | 0.140 | 0.164 | 0.192 | 0.223 | 0.259 | 0.300 | 0.346 |
| 50% | 0.045 | 0.054 | 0.065 | 0.077 | 0.092 | 0.108 | 0.127 | 0.149 | 0.174 | 0.203 | 0.236 | 0.273 | 0.315 |
| 55% | 0.041 | 0.049 | 0.058 | 0.070 | 0.082 | 0.097 | 0.115 | 0.134 | 0.157 | 0.183 | 0.212 | 0.245 | 0.283 |
| 60% | 0.036 | 0.043 | 0.052 | 0.062 | 0.073 | 0.087 | 0.102 | 0.119 | 0.140 | 0.162 | 0.189 | 0.218 | 0.252 |
| 65% | 0.032 | 0.038 | 0.045 | 0.054 | 0.064 | 0.076 | 0.089 | 0.104 | 0.122 | 0.142 | 0.165 | 0.191 | 0.220 |
| 70% | 0.027 | 0.033 | 0.039 | 0.046 | 0.055 | 0.065 | 0.076 | 0.090 | 0.105 | 0.122 | 0.141 | 0.164 | 0.189 |
| 75% | 0.023 | 0.027 | 0.032 | 0.039 | 0.046 | 0.054 | 0.064 | 0.075 | 0.087 | 0.102 | 0.118 | 0.136 | 0.157 |
| 80% | 0.018 | 0.022 | 0.026 | 0.031 | 0.037 | 0.043 | 0.051 | 0.060 | 0.070 | 0.081 | 0.094 | 0.109 | 0.126 |
| 85% | 0.014 | 0.016 | 0.019 | 0.023 | 0.027 | 0.032 | 0.038 | 0.045 | 0.052 | 0.061 | 0.071 | 0.082 | 0.094 |
| 90% | 0.009 | 0.011 | 0.013 | 0.015 | 0.018 | 0.022 | 0.025 | 0.030 | 0.035 | 0.041 | 0.047 | 0.055 | 0.063 |
| 95% | 0.005 | 0.005 | 0.006 | 0.008 | 0.009 | 0.011 | 0.013 | 0.015 | 0.017 | 0.020 | 0.024 | 0.027 | 0.031 |

FIGURE 12

Maximum Vapor Caculation
Gallons Per hour

Blower CFM 1000
Coff 4.00

| Humidity | Temp F 40 | 45 | 50 | 55 | 60 | 65 | 70 | 75 | 80 | 85 | 90 | 95 | 100 |
|---|---|---|---|---|---|---|---|---|---|---|---|---|---|
| 40% | 0.788 | 0.945 | 1.130 | 1.344 | 1.594 | 1.882 | 2.214 | 2.596 | 3.033 | 3.531 | 4.099 | 4.742 | 5.470 |
| 45% | 0.722 | 0.867 | 1.036 | 1.232 | 1.461 | 1.725 | 2.030 | 2.379 | 2.780 | 3.237 | 3.757 | 4.347 | 5.014 |
| 50% | 0.657 | 0.788 | 0.941 | 1.120 | 1.328 | 1.568 | 1.845 | 2.163 | 2.527 | 2.943 | 3.416 | 3.952 | 4.558 |
| 55% | 0.591 | 0.709 | 0.847 | 1.008 | 1.195 | 1.411 | 1.661 | 1.947 | 2.275 | 2.649 | 3.074 | 3.557 | 4.103 |
| 60% | 0.525 | 0.630 | 0.753 | 0.896 | 1.062 | 1.255 | 1.476 | 1.731 | 2.022 | 2.354 | 2.732 | 3.161 | 3.647 |
| 65% | 0.460 | 0.551 | 0.659 | 0.784 | 0.930 | 1.098 | 1.292 | 1.514 | 1.769 | 2.060 | 2.391 | 2.766 | 3.191 |
| 70% | 0.394 | 0.473 | 0.565 | 0.672 | 0.797 | 0.941 | 1.107 | 1.298 | 1.516 | 1.766 | 2.049 | 2.371 | 2.735 |
| 75% | 0.328 | 0.394 | 0.471 | 0.560 | 0.664 | 0.784 | 0.923 | 1.082 | 1.264 | 1.471 | 1.708 | 1.976 | 2.279 |
| 80% | 0.263 | 0.315 | 0.377 | 0.448 | 0.531 | 0.627 | 0.738 | 0.865 | 1.011 | 1.177 | 1.366 | 1.581 | 1.823 |
| 85% | 0.197 | 0.236 | 0.282 | 0.336 | 0.398 | 0.470 | 0.554 | 0.649 | 0.758 | 0.883 | 1.025 | 1.186 | 1.368 |
| 90% | 0.131 | 0.158 | 0.188 | 0.224 | 0.266 | 0.314 | 0.369 | 0.433 | 0.505 | 0.589 | 0.683 | 0.790 | 0.912 |
| 95% | 0.066 | 0.079 | 0.094 | 0.112 | 0.133 | 0.157 | 0.185 | 0.216 | 0.253 | 0.294 | 0.342 | 0.395 | 0.456 |

FIGURE 13

LIQUID PRODUCT VAPORIZING APPARATUS FOR AN AIR DEODORIZING SYSTEM

CROSS REFERENCE TO RELATED APPLICATIONS

This application is a continuation-in-part of U.S. patent application Ser. No. 09/224,647, filed Dec. 31, 1998 abandoned, which claims the benefit of U.S. Provisional Application No. 60/070,357, filed Jan. 2, 1998.

BACKGROUND OF THE INVENTION

1. Field of the Invention

The present invention relates generally to the field of odor control. More specifically, the present invention relates to the vaporization of odor neutralizing products and the transfer of such vaporized products to malodorous areas for masking and elimination of malodors.

2. Related Art

Air pollution is of great concern to the modem world. Pollution of the air is characterized by offensive odors and/or toxic fumes that are a nuisance to humans living near or traveling through the polluted areas (both offensive odors and gases with other polluting or negative properties such as toxicity are hereinafter referred to as "malodors"). Unfortunately, air pollution is often the result of an activity deemed valuable to our modern world. Examples of valuable activities that produce malodors include sewage and wastewater treatment, chemical manufacturing, agricultural and livestock fanning, waste incineration, and petroleum refinement. Rather than completely eliminate these valuable endeavors, society has decided to simply control or regulate the malodors produced from many air polluting activities, thereby retaining the benefit from the activities while greatly reducing the negative effects upon human life.

Scrubbers and electrostatic precipitators have been used in many malodorous systems to control pollution released into the open air. Scrubbers and electrostatic precipitators achieve pollution control by removing odors and other polluting impurities from system exhaust gas streams. In a scrubber system, exhaust gasses containing odorous particles such as sulfides are introduced to a precipitant such as sulfuric acid. Introduction of the odorous particles to the precipitant causes the odorous particles to bond with the precipitant and form a solid precipitate. The solid precipitate particles fall from the exhaust gas to the floor of the scrubber where they may be easily removed. By causing the odorous particles to fall to the floor of the scrubber, malodors are removed from the exhaust gas stream.

Similarly, electrostatic precipitators remove liquid or solid pollution particles suspended in an exhaust gas by ionizing the suspended particles and subjecting the charged particles to an electrode. The ionized particles are attracted to the electrode, where they are captured and removed from the exhaust gas, thus removing the malodor from the exhaust gas stream.

Unfortunately, scrubbers and electrostatic precipitators are generally limited to industrial activities because they can not be used to control malodors that are not contained within an exhaust gas stream of a closed system. Examples of systems where malodors are not contained within an exhaust gas stream include sewage pits, garbage dumps, and pig farms. Furthermore, there are some industrial systems that produce malodorous exhaust gasses which are difficult for scrubbers and electrostatic precipitators to control because of ineffective precipitants or ionization techniques.

Another method of controlling malodors involves masking the malodor with a pleasant aromatic liquid or neutralizing the malodor with an enzyme or catalyst. One method which has been suggested uses a distribution system including at least one vapor delivery air duct having a longitudinal series of vapor release ports extending over and around an odor source such a sewage treatment tank or a garbage dump. A blower pumps a stream of vapor-laden air through the duct and out of the release ports. Deodorizing liquid product is pumped to the system through an atomizing nozzle or a copper tube having a plurality of holes which release minute droplets of the deodorizing liquid product into the air stream. The liquid product is vaporized to some extent by the impact of the air stream on the droplets. Liquid product that is not vaporized is lost as the droplets fall out of the air stream and through holes located in the air duct or distribution pipes. A typical problem with this type of system is that vaporization of the liquid product is highly inefficient. Testing has shown that, under the best of conditions, only about 28 percent of the liquid product sprayed out of the atomizing nozzle or copper tube is vaporized and used by the system. A considerable amount of the remaining liquid product is often blocked from exiting the air duct, and the inefficiency of the system is compounded because the accumulated liquid product in the duct obstructs air flow.

Another distribution system vaporizes liquid deodorizing product by bubbling air through the liquid product. This bubbling action causes a vapor to rise from the liquid product. The vapor rising from the liquid product is passed to the air duct where it is eventually delivered to the malodor area. Because the system does not utilize an atomizing nozzle, liquid product is not sprayed into the air duct and no collection of liquid product occurs within the air duct. Nevertheless, this system is not effective for several malodorous applications because the bubbling system does not readily vaporize a sufficient quantity of certain deodorizing products and consequently is incapable of delivering sufficient quantities of the deodorizing product to an odor source to overcome the malodor.

Still other systems are designed to deliver liquid deodorant mist to a malodor area by the use of many nozzles in a multiple cluster system. In these systems, each nozzle directly distributes a spray mist of the liquid deodorant product into the malodor source. An example of such a system has been employed in a 100 ton per hour asphalt plant in Grand Rapids, Mich. where multiple nozzles spray liquid deodorant directly into a pollution containing stack to control the odor emanating from the stack. These types of open air spray systems tend to be very inefficient because much of the liquid deodorant is lost as it falls to the ground and does not vaporize and mix with the malodor. Additionally, the multiple nozzles used in these systems are costly and difficult to maintain. There is a tendency for the nozzles in these systems to clog or plug and deliver inconsistent rates of product to the malodorous area.

Accordingly, it is a primary object of the present invention to overcome many of the above deficiencies by efficient vaporization of liquid deodorant products and delivery of such vaporized products to a malodorous area without significant loss of the liquid deodorant products.

Another object of the present invention is to efficiently vaporize a vast array of liquid deodorizing products for delivery to a wide range of odor producing areas.

It is another object of this invention to provide a deodorizing system that is simple to install, reliable, easy to operate and maintain and competitively priced.

SUMMARY OF THE INVENTION

A primary objective when utilizing odor neutralizing chemicals is to provide for complete mixing of the odor neutralizing chemicals with the malodors, thus forcing a chemical reaction between the malodors and the neutralizing chemicals. To accomplish this, the present invention efficiently vaporizes odor-neutralizing liquid deodorants and distributes the vaporized deodorants into malodorous areas where the vaporized deodorants are readily mixed with the malodors to neutralize the malodors or otherwise render them harmless.

The invention comprises an inlet channel, a vaporization chamber, an air blower, and distribution pipes. Fresh ambient air is drawn into the system and through the inlet channel by the air blower, thus creating a stream of air flowing through the system. The stream of air is directed to the vaporization chamber where an atomizing nozzle sprays atomized liquid product into the vaporization chamber. Within the vaporization chamber, the atomized liquid product is vaporized and becomes entrained in the air stream flowing through the chamber, making the air stream a "treated" air stream. The treated air stream then flows through distribution pipes to a plurality of vapor release ports which allow the treated air to be released into the malodorous area.

The atomizing nozzle includes a tip for spraying atomized liquid deodorant from the nozzle and into the air stream. The atomizing nozzle receives a stream of pressurized air from an air pump and a stream of liquid deodorant from a liquid reservoir. The liquid deodorant may either be pulled from the liquid reservoir under a vacuum created by the atomizing nozzle (e.g., a siphoning nozzle), or it may be pumped into the atomizing nozzle by means of a metering pump which delivers product to the atomizing nozzle at a precise rate. The force of the air being pushed through the nozzle by the air pump causes the liquid deodorant to be atomized as it exits the atomizing nozzle.

Release of the liquid deodorant from the atomizing nozzle results in a very fine mist of minute droplets generally in the approximate range of between 20 and 50 microns and even smaller. Air pressure to the atomizing nozzle may be increased or decreased to adjust the size of liquid deodorant particles leaving the nozzle. As the air pressure increases, the size of liquid deodorant particles decrease, and vice-versa. As the mist is injected into the vaporization chamber, it is believed that many of the minute droplets vaporize immediately, possibly due in part to a lower pressure upon the particles upon leaving the atomizing nozzle and entering the vaporization chamber.

The vaporization chamber includes a top, a bottom, and a sidewall, as well as a chamber inlet and outlet to allow the air stream to flow through the chamber. The size of the vaporization chamber will vary depending upon the required output of the siphoning or spray nozzle. Larger vaporization chambers will be required for treatment applications requiring a greater rate of liquid deodorant delivery to the malodorous area. It is believed that the liquid-in-gas dispersion formed within the vaporization chamber is such that many of the fine liquid particles of deodorizer product stay in suspension and readily evaporate, or "vaporize", their state changing from a liquid to a gas. Most of the larger and heavier liquid particles coalesce, condense and collect on the vaporization chamber walls or fall to the vaporization chamber floor. This larger liquid particle separation may be enhanced by providing a change in direction of the air stream or by providing a vaporization chamber having a closed end, i.e., an end having no chamber inlet or outlet. The excess liquid deodorant collected on the vaporization chamber walls is returned by gravity to the liquid reservoir. To this end the vaporization chamber is generally sloped toward the liquid reservoir so that liquid deodorant flows down the walls of the vaporization chamber and into the liquid reservoir. Accordingly, a large percentage of un-vaporized liquid deodorant is removed from the air stream by the vaporization chamber and returned to the liquid reservoir for re-use, thus minimizing the loss of liquid deodorant downstream from the nozzle, and increasing the efficiency of the system.

After leaving the vaporization chamber, the treated air stream (i.e. untreated air and vaporized deodorant) is routed through air ducts to the air blower. The air blower not only draws untreated air through the system, but also forces the treated air through the distribution pipes. The distribution pipes carry the treated air to various vapor release ports which distribute the treated air into or around odor producing areas. The treated air contains sufficient vapors to overcome and/or neutralize existing offensive odors in the malodorous area.

Accordingly, the present invention provides for more efficient vaporization of liquid deodorants and more effective delivery of the deodorants in vapor form to malodorous areas without significant loss of the liquid deodorant.

Additionally, the present invention provides for vaporization of a wide range of liquid deodorants for delivery to various malodorous areas.

Furthermore, because of its relatively simple design, the present invention provides an air deodorizing system that is simple to install, reliable, easy to operate and maintain, and is competitively priced.

BRIEF DESCRIPTION OF THE DRAWINGS

FIG. 11 is a chart showing the amount of liquid deodorant that may be vaporized at various temperatures and humidities at a particular air flow rate;

FIG. 12 is a chart showing the amount of liquid deodorant that may be vaporized at various temperatures and humidities at another air flow rate;

FIG. 13 is a chart showing the amount of liquid deodorant that may be vaporized at various temperatures and humidities at still another air flow rate;

DETAILED DESCRIPTION

Figure 1:
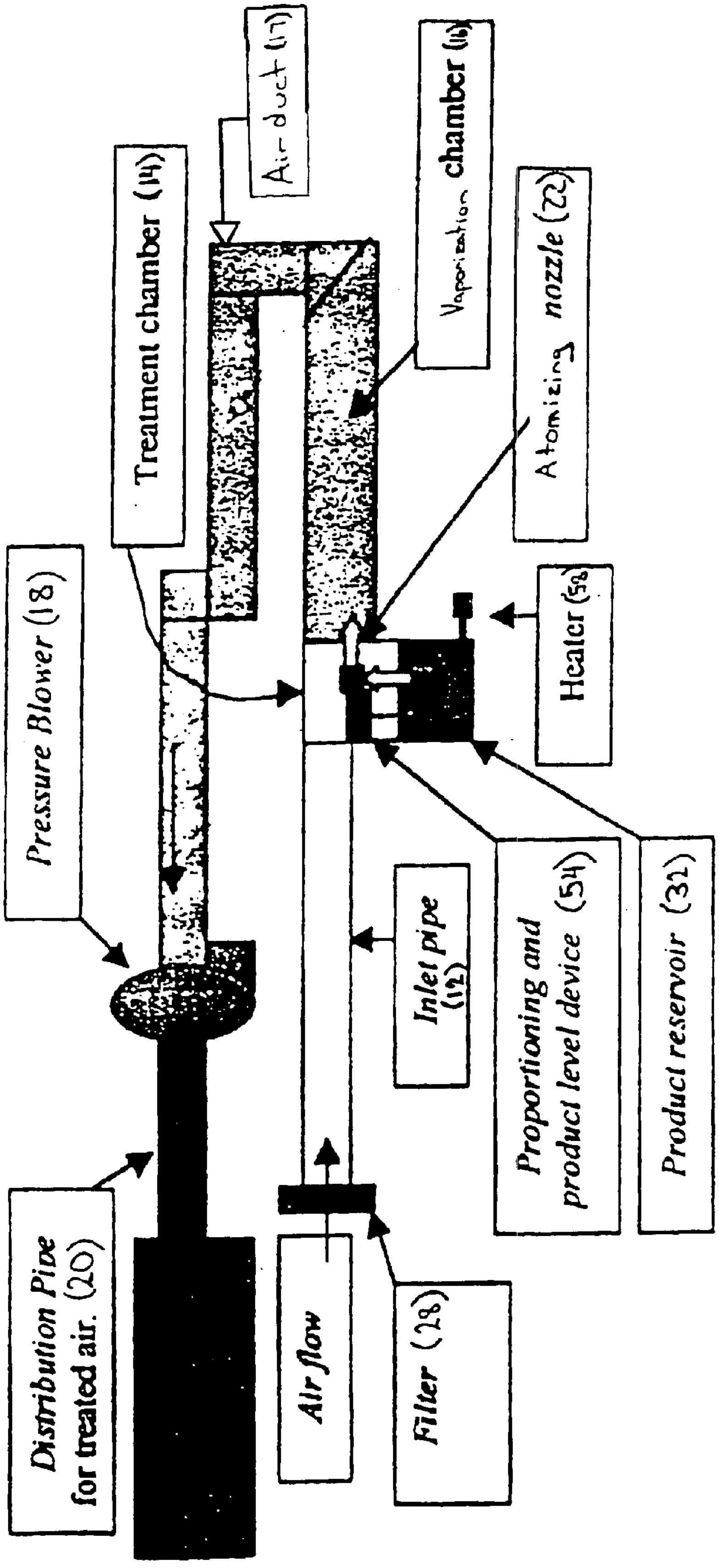
FIG. 1 shows a plan view for the liquid product vaporizing apparatus of the present invention.
Figure 2:
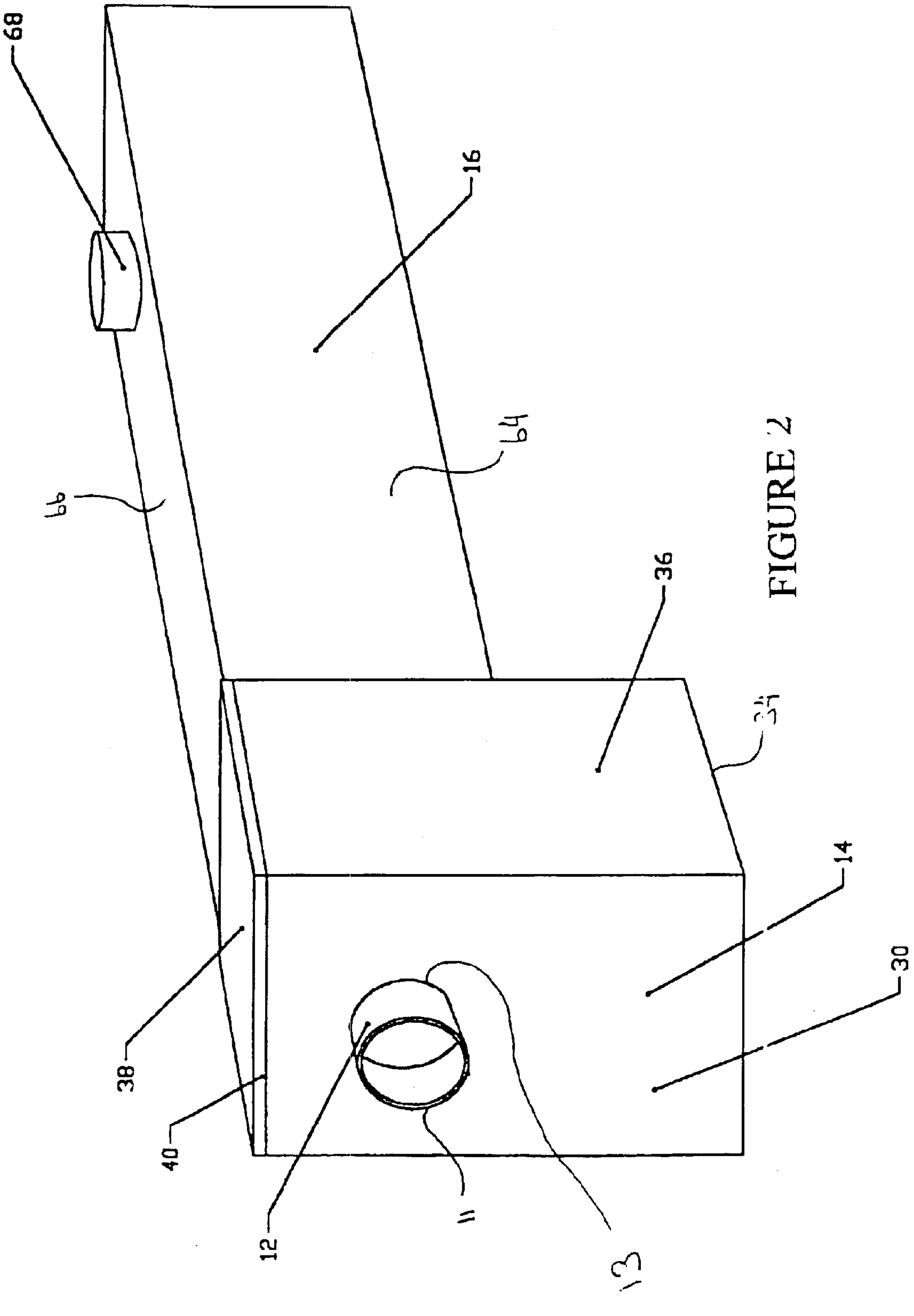
FIG. 2 shows an exterior perspective view of a vaporization chamber.
Figure 3:
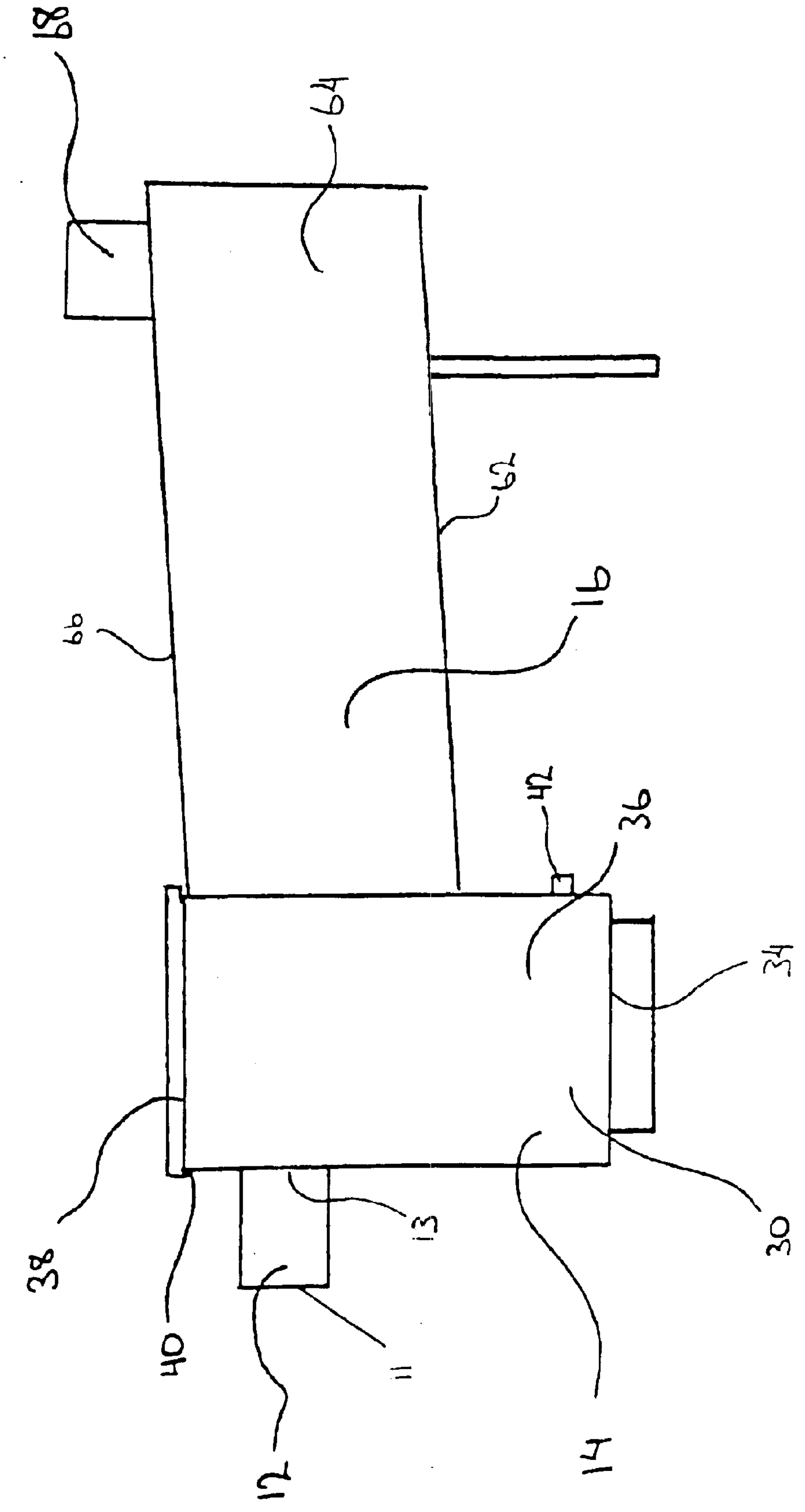
FIG. 3 shows an elevational side view of the vaporization chamber.
Figure 4:
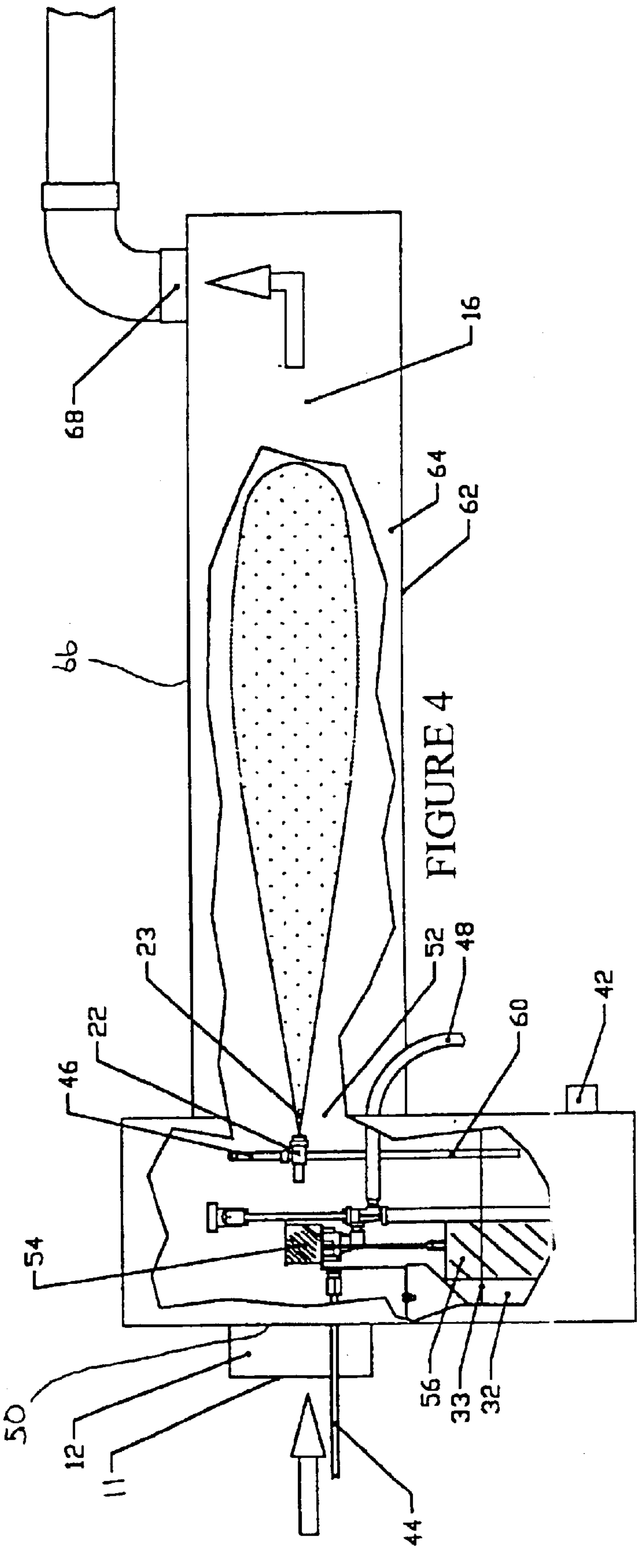
FIG. 4 shows a sectional side view of the vaporization chamber.

Referring to FIGS. 1–5, a vapor distribution system 10 is disclosed for use in treating malodorous areas 5 with a deodorant, bacterial digestant, or other such odor controlling compounds or products (referred to herein as "liquid deodorants"). The vapor distribution system 10 comprises an air intake port 12, a treatment chamber 14, a vaporization chamber 16, an air duct 17, a pressure blower 18, and at least one distribution pipe 20 for treated air. Operation of the blower 18 draws ambient fresh air into the air intake port 12 and creates an air stream within the system 10. The air stream flows through the treatment chamber 14 where a liquid deodorant is introduced into the air stream as a mist by a nozzle 22, which sprays the mist into the vaporization chamber 16. As the air stream moves through the vaporization chamber 16, the liquid deodorant is vaporized and dispersed into the air stream. The air stream containing vaporized deodorant is then passed though the pressure blower 18 and forced through the distribution pipes 20. The vapor distribution pipes include a series of vapor release ports 26 for delivery of the vaporized deodorant to a malodorous area.

The air intake port 12 is made of polyvinyl chloride (PVC) or stainless steel material and includes a receiving end 11 and a chamber end 13. An air filter 28 may be incorporated on the receiving end 11 of the air intake port 12 upstream of the treatment chamber 14 for removing debris and other particles from the air stream. The air filter 28 helps to keep the vapor distribution system clean and free of solid objects that may enter any of the various chambers and pipes of the vapor distribution system 10 and clog or otherwise cause problems within the system, particularly at the release ports 26. The chamber end 13 of the air intake port 12 is connected to the treatment chamber.

The treatment chamber 14 is made of stainless steel or PVC and includes a housing 30 and a liquid deodorant reservoir 32. The housing includes a vessel bottom wall 34, a vessel side wall 36 sealingly joined to vessel bottom wall 34, and a vessel lid 38. The lid 38 is positioned over the housing to provide access to the liquid deodorant reservoir from the top of the treatment chamber. The lid 38 is preferably mounted on hinges 40 and has a handle to provide easier access to the deodorant reservoir. The side wall 36 further includes a drain spigot 42 for draining liquid deodorant from the reservoir, a liquid supply line (not shown) for feeding liquid to the reservoir, an air supply line 46 entrance for feeding pressurized air into the treatment chamber, and a deodorant supply tube entrance for feeding concentrated liquid deodorant into the reservoir. A treatment chamber entrance 50 and a vaporization chamber inlet 52, or intake port, are also formed in side wall 36 to allow the air stream to pass through the treatment chamber 14 and into the vaporization chamber 16.

A quantity of liquid deodorant is retained within the liquid deodorant reservoir 32, having an upper liquid surface line 33 located substantially below the treatment chamber entrance 50 and vaporization chamber inlet 52. The liquid deodorant used for delivery to the malodorous area is either a liquid masking agent or a liquid odor neutralizing agent. Examples of such agents include MAXIM SP 798 enzyme fortified bacterial digestant I deodorant manufactured by Midlab, Inc. of Sweetwater, Tenn., and ECOSORB® natural odor control manufactured by Odor Management, Inc. of Minneapolis, Minn. A preferred neutralizing agent is one including enzymes and a catalyst, which biologically reacts with odor-causing molecules such as ammonia and hydrogen sulfide, and which attacks various odor-producing microbes. The liquid deodorant is retained in a supply vessel such as a fifty-five gallon drum, five gallon bucket or one gallon jug.

A product maintenance device 54 keeps the deodorant level substantially constant at the upper liquid surface line 33. The product maintenance device is controlled by a float 56 and electric switch system which automatically operates an electric supply line valve to maintain the liquid in the reservoir at a desired level. When the supply line valve is opened, water flows into the reservoir through a liquid supply line (not shown). As the water flows into the reservoir, concentrated liquid deodorant is proportionally siphoned from the supply vessel and delivered to the reservoir through the supply tube 48. Accordingly, the product maintenance device not only acts as a liquid level control for the liquid deodorant within the reservoir, but also properly delivers a desired concentration of the liquid deodorant to the deodorant reservoir. The proportion of water to liquid deodorant within the product reservoir is generally selected between 1:1 and 99:1. Should the desired concentration of liquid deodorant change, an inlet orifice on the product maintenance device may be removed and a new inlet orifice may be inserted which delivers the desired concentration of liquid deodorant to the deodorant reservoir.

In addition to the product maintenance device, the treatment chamber may also be equipped with other maintenance devices such as a thermometer and/or a heater 58. The thermometer and heater combination may be desired for outdoor applications of the vapor distribution system where freezing of the liquid deodorant reservoir is a concern.

The nozzle 22 is positioned within the liquid deodorant reservoir at a prescribed height above the upper liquid surface line. The nozzle includes a tip, or nozzle release point 23, positioned to spray through the chamber opening in the same direction as the air stream and directly into the vaporization chamber. The nozzle 22 is fed with pressurized air from the air supply line 46, which is joined to an air pump located outside of the treatment chamber 14. The nozzle uses the pressurized air to distribute tiny particles of the liquid deodorant from the nozzle tip 23.

Pressurized air flowing through the siphoning nozzle may also be used to siphon liquid deodorant from the deodorant reservoir through a siphon tube 60 which extends from the nozzle to below the upper liquid surface line. Alternatively, the nozzle may receive liquid deodorant through a pump tube, which is used along with a metering pump to distribute liquid deodorant to the nozzle at a precise rate. A deodorant filter is located within the siphon tube or pump tube to remove solid particles of liquid deodorant that may clog the nozzle. After passing through the deodorant filter, the liquid deodorant is sprayed from the nozzle 22 as a mist into the air stream.

If a siphoning nozzle is used, several factors will control the amount of liquid deodorant that is distributed to the vaporization chamber from the nozzle. First, the amount of liquid deodorant sprayed from the nozzle is dependent upon the type and model of nozzle 22. Larger nozzles will generally siphon liquid deodorizer from the product reservoir at a faster rate than smaller nozzles, therefore injecting more liquid deodorizer into the vaporization chamber. Second, the amount of liquid deodorant distributed to the vaporization chamber is dependent upon the amount of pressure produced by the air pump and delivered to the nozzle. Greater air pressure applied to the nozzle will cause a greater amount of liquid deodorizer to be sprayed from the nozzle and into the vaporization chamber. Third, the amount of liquid deodorant provided is dependent upon the distance between the nozzle 22 and the upper liquid surface line 33 of the product reservoir. The closer the nozzle is to the upper liquid surface line, the more deodorant will be distributed from the nozzle. Fourth, the greater the concentration of the liquid deodorant contained in the product reservoir the greater the amount of liquid deodorant that will be provided to the vaporization chamber. Of course, if a single nozzle is not capable of providing a sufficient amount of liquid deodorant to the vaporization chamber, multiple nozzles may be used.

As an example of the above, consider a particular siphoning nozzle where 20 psi of air pressure is applied to the nozzle which is positioned 12" above the upper liquid deodorant surface line and the nozzle sprays 0.33 gallon per hour of liquid deodorant into the vaporization chamber. If the air pressure is increased, the flow rate of the liquid deodorant will also increase. If the prescribed height above the upper liquid deodorant surface is increased, the flow rate of the liquid deodorant will decrease.

The nozzle 22 is easily accessible though the lid 38 of the treatment chamber 14. Accordingly, the nozzle may be easily replaced should a problem arise with the nozzle. Preferably the nozzle is self-cleaning to avoid complete replacement of the nozzle. Self cleaning nozzles typically provide for easy cleaning with an automatic blast of air that is activated periodically by the nozzle itself or by manual depression of a cleaning button. An example of a preferred siphoning nozzle for use with the vapor distribution system is the DELEVAN® ¼ ALX-07 air atomizing series spray nozzle. Of course, other brands of atomizing/siphoning nozzles may be appropriate for use in the present invention.

The vaporization chamber is made of stainless steel or other suitable material such as PVC and comprises a chamber floor 62, a side wall 64, a chamber ceiling 66 and a chamber outlet 52. The chamber floor 62 is integral with the bottom of the chamber inlet 52 at a proximate end of the chamber floor 62 and is inclined upward toward a distal end of the floor 62. Because the chamber floor 62 is inclined, the chamber floor provides a liquid deodorant recovery means which returns un-vaporized liquid deodorant to the deodorant reservoir through the chamber opening. The chamber outlet 52 is located on a distal end of the chamber ceiling from the treatment chamber 14. The chamber inlet 52 is situated on the side wall 64 and connects the treatment chamber 14 to the vaporization chamber 16.

The vaporization chamber 16 is designed to provide sufficient time and space for the liquid deodorant mist to be vaporized within the vaporization chamber before exiting the vaporization chamber. In other words, the vaporization chamber must be of sufficient size to contain the mixture of air and liquid deodorant mist for a sufficient time for much of the liquid deodorant mist to vaporize before exiting the vaporization chamber. Accordingly, the volumetric size of the vaporization chamber is dependent upon several factors including type of liquid deodorant to be vaporized, the flow rate of the air stream within the system, and gallons per hour of deodorant to be vaporized. In one vapor distribution system that has been operated successfully, an air stream flow rate of 800 c.f.m. required a 1'×1'×4' vaporization chamber to vaporize and deliver 0.3 gallons per hour of deodorant. For vaporizing and delivering 1 gallon per hour of deodorant at the same flow rate, a vaporization chamber having a 16 inch square cross section and a length of 6 feet was required. The diameter of the vaporization chamber air stream exit is typically 6 inches in diameter, but this may also vary according to the size of the vaporization chamber and job to be performed.

The air stream exit to the vaporization chamber leads through a portion of air duct 17 to a pressure blower 18. The portion of air duct 17 extending from the air stream exit is typically smaller than the width or diameter of the vaporization chamber and generally the same diameter as the air stream exit. A typical air duct 17 may be 6" in diameter and comprised of PVC, stainless steel, or other material suitable for channeling of the air stream.

The pressure blower 18 comprises an air input side, an air output side, and a large fan, wheel, or other air moving device. The pressure blower causes air to be drawn to the air input side and exhausted from the air output side. This movement of air through the fan results in an air stream flow rate, which may be measured in cubic feet per minute (c.f.m.). Typical air stream flow rates for the vapor distribution system 10 are between 600 and 2000 c.f.m. The blower 18 is preferably a radial wheel or high pressure blower such as that produced by NEW YORK BLOWER. The blower 18 may be driven by either a diesel engine or an electric motor.

A plurality of distribution pipes are connected to the air output side of the pressure blower. The distribution pipes are generally composed of PVC or similar corrosion resistant material. The distribution pipes 20 include vapor release ports 26 at various locations to allow the vaporized deodorant to be delivered to the malodorous area 5. At least one end cap 24 may be provided to seal off the ends of the distribution pipes and force the vapor through the ports.

The desired rate at which liquid deodorant is vaporized and delivered to the malodorous area 5 will depend upon the particular application. For example, a landfill may require 0.4–0.5 gallons per hour of vaporized liquid deodorant to neutralize malodors, while the digester tank of a wastewater treatment plant may only require the delivery of 0.1–0.2 gallons per hour to neutralize malodors. A variety of factors will determine whether the desired amount of liquid deodorant is actually vaporized by the system and delivered to the malodorous area. These factors include the following:

the temperature of the air entering the system;

the humidity of the air entering the system;

the rate of air flowing through the system;

the droplet size produced by the nozzle; and the volatility of the particular liquid deodorant to be vaporized.

The temperature and humidity of the air stream plays a large role in determining the amount of liquid deodorant that will be vaporized into the air stream and delivered to the malodorous area Relative humidity is the amount of water vapor in the air compared with the amount of vapor needed to make the air saturated at a the current air temperature. The quantity of water that air can "hold" is dependent upon the temperature of the air. Colder air is capable of "holding" less water vapor than warmer air. As the temperature of a unit of air drops, the relative humidity of the unit of air will rise and the air will be able to hold less water. If the temperature drops to the dew-point (relative humidity of 100%), the air becomes saturated and condensation occurs. Accordingly, the present invention will vaporize less liquid deodorant per unit of air flowing through the system as the temperature decreases and the relative humidity increases.

As the temperature decreases and the relative humidity of the air increases, a greater quantity of air will need to flow through the system in order for the liquid deodorant to be vaporized at the desired rate. In these situations, the blower must be capable of drawing air into the system at a faster rate. In addition, vaporization of the liquid deodorant may also be encouraged by decreasing the size of the particles sprayed from the nozzle. The specifications of the nozzle used in the system will determine how small the particles sprayed from the nozzle will be. Increasing the pressure of the air forced through the nozzle will generally cause smaller particles to be sprayed from the nozzle.

FIGS. 11–13 show maximum vaporization rates for the system 10, depending on the temperature and humidity of the air at a particular air stream flow rate. FIG. 11 displays the maximum vaporization rates when the air flow rate is 829 c.f.m., FIG. 12 shows the maximum vaporization rates when the air flow rate is 69 c.f.m., and FIG. 13 shows the maximum vaporization rates when the air flow rate is 1000 c.f.m. To calculate a vaporization rate for a particular temperature in and relative humidity, the following formulas are used:

First, the actual vapor pressure (P) is calculated in Pascals, $$P=(C*10^{(7.5*Tdc/(237.7+Tdc))}*100;$$

Next, the vapor density (D) is calculated in Kg/m$^3$, $$D=P/(T_k+R_w);$$

Finally, the gallons per hour vaporized ($G_v$) is calculated, $$G_v=D*F*60/133;$$

where C=the system coefficient (which is a function of nozzle type, nozzle air pressure, ground elevation where the system is located, and volatility of the liquid deodorant being vaporized), $T_{dc}$ is the dew point temperature in degrees Celsius, $T_k$ is the air temperature in degrees Kelvin, $R_w$ is the gas constant for water vapor (461.5 J/kg*Kelvin), and F=the air stream flow rate. Each of the charts shown in FIGS. 11–13 assume that the system coefficient is 4.0, which is common for a typical nozzle receiving 30 psi of air pressure from the air pump and distributing a liquid deodorant with a typical volatility, such as ECOSORB®. If higher liquid deodorant rates are desired at a particular air flow rate, the system coefficient must be increased. This may be easily accomplished by increasing the nozzle air pressure, but the nozzle pressure may only be increased as high as the maximum air pressure allowed by the nozzle specifications.

Operation of the vapor distribution system 10 may be triggered by manual or automatic control. For automatic control, an electronic control system is used having at least one sensing instrument for measuring an external condition such as time, atmospheric pressure, temperature, humidity, wind direction, wind velocity, etc. The electronic control system receives information from the sensing instrument and enables or disables the vapor distribution system 10 based upon external conditions meeting a prescribed criteria. For example, the electronic control system may trigger operation of the vapor distribution system 10 when the winds are blowing from the east or north, but disable the vapor distribution system 10 when the winds are blowing from the west or south.

The vapor distribution system 10 is enabled upon activation of the pressure blower 18 which draws untreated air into the air intake port 12. The air drawn into the air intake port 12 creates an air stream within the vapor distribution system 10. The air stream is passed through the air filter 28 to remove particulate matter from the air stream that could be damaging to the system. Next, the air stream enters the treatment chamber 14 where a mist of liquid deodorant is sprayed into the air stream from the nozzle 22. The air stream then passes through the chamber inlet 52 and into the vaporization chamber 16.

Much of the liquid deodorant distributed to the vaporization chamber 16 will be vaporized within the vaporization chamber. Remaining un-vaporized particles of liquid deodorant form on the vaporization chamber side wall 64 and fall to the chamber floor 62. The un-vaporized liquid deodorant eventually returns to the deodorant reservoir 32 as gravity draws the deodorant to the chamber floor 62, down the incline of the chamber floor 62, through the chamber inlet 52 and into the deodorant reservoir 32. The air stream exiting the vaporization chamber 16 contains treated air comprised of fresh ambient air and vaporized deodorant along with a small portion of tiny suspended particles of liquid deodorant.

Figure 5:
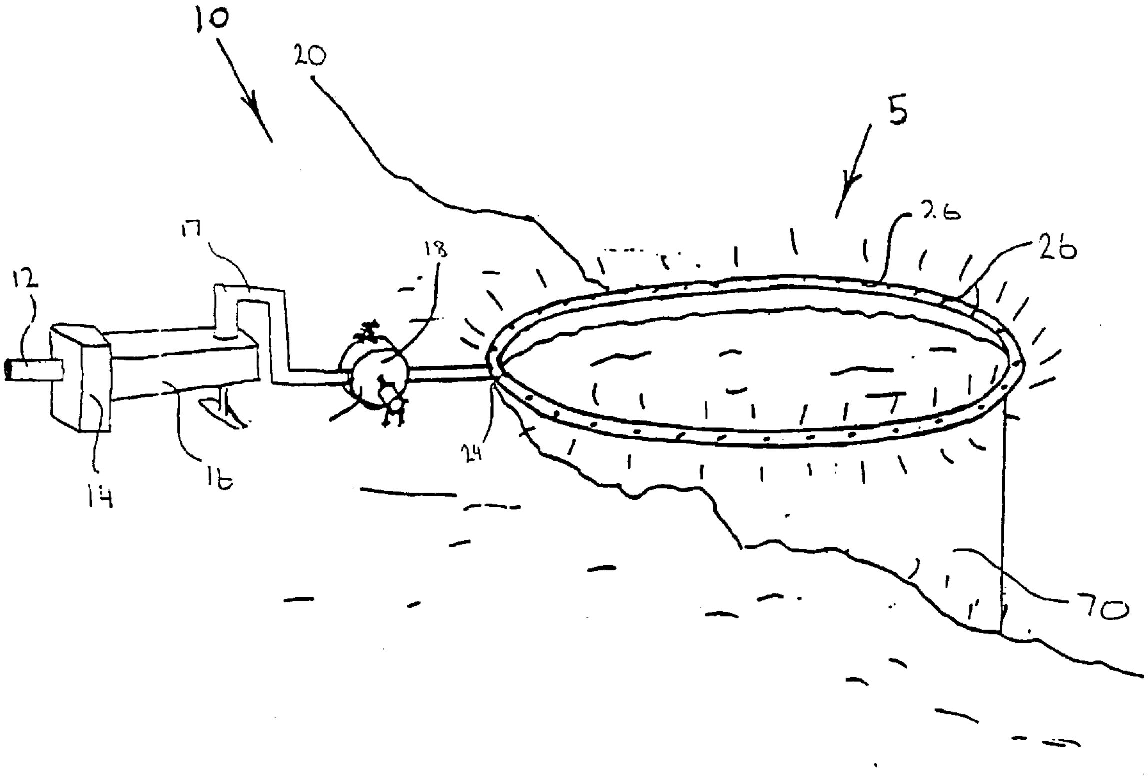
FIG. 5 shows a perspective view of the liquid product vaporizing apparatus according to the present invention.
Figure 6:
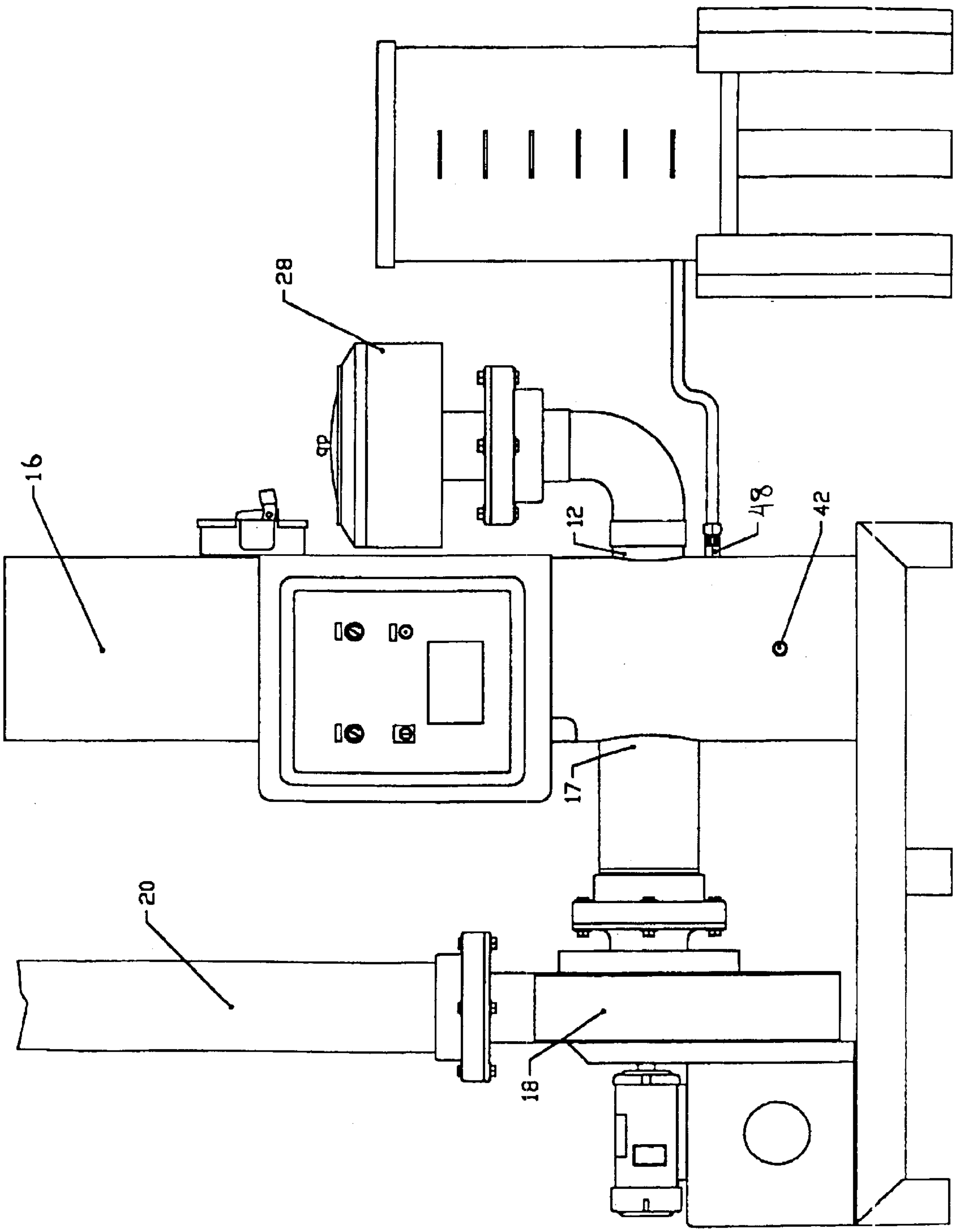
FIG. 6 shows a plan view of an alternative embodiment of the liquid product vaporizing apparatus having a vertical vaporization chamber.

Treated air flows up through the vaporization chamber outlet 52 and is routed by air ducts 17 to the pressure blower 18. The treated air is drawn to the fan of the pressure blower 18, passes through the fan of the pressure blower, and is then forcibly pushed through the distribution pipes 20 and out the vapor release ports 26 to condition an odor source 5. As shown in FIG. 5, the odor source 5 might be an open tank 70, such as sewage treatment plant tank, and the distribution pipes 20 may be deployed along and around the perimeter of the open tank 70 to generate an air curtain of vaporized deodorant around the odor source 5.

Figure 7:
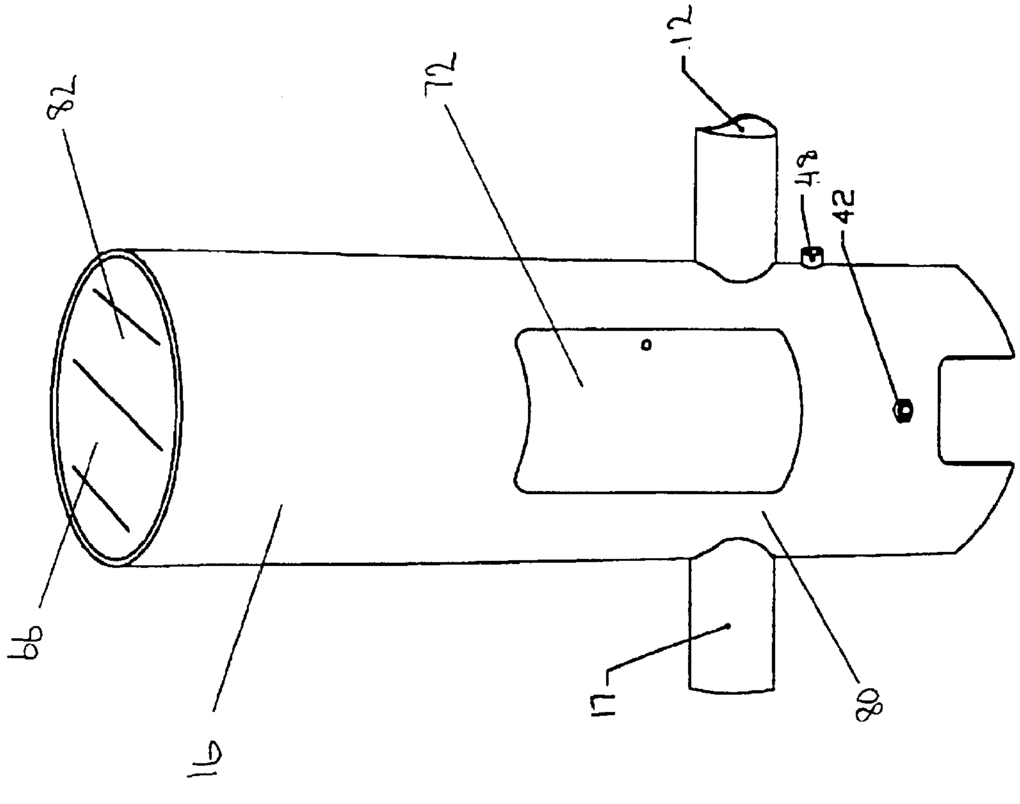
FIG. 7 shows an exterior perspective view of the vertical vaporization chamber.
Figure 9:
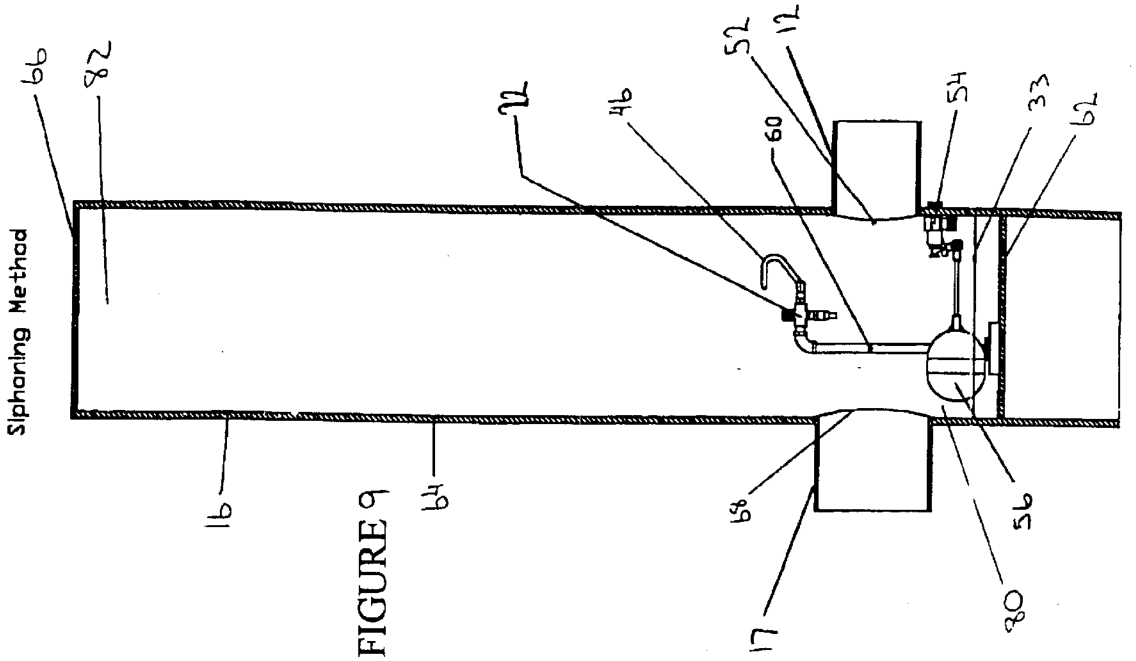
FIG. 9 shows a sectional side view of the vertical chamber including a siphoning nozzle for liquid deodorant transfer.
Figure 8:
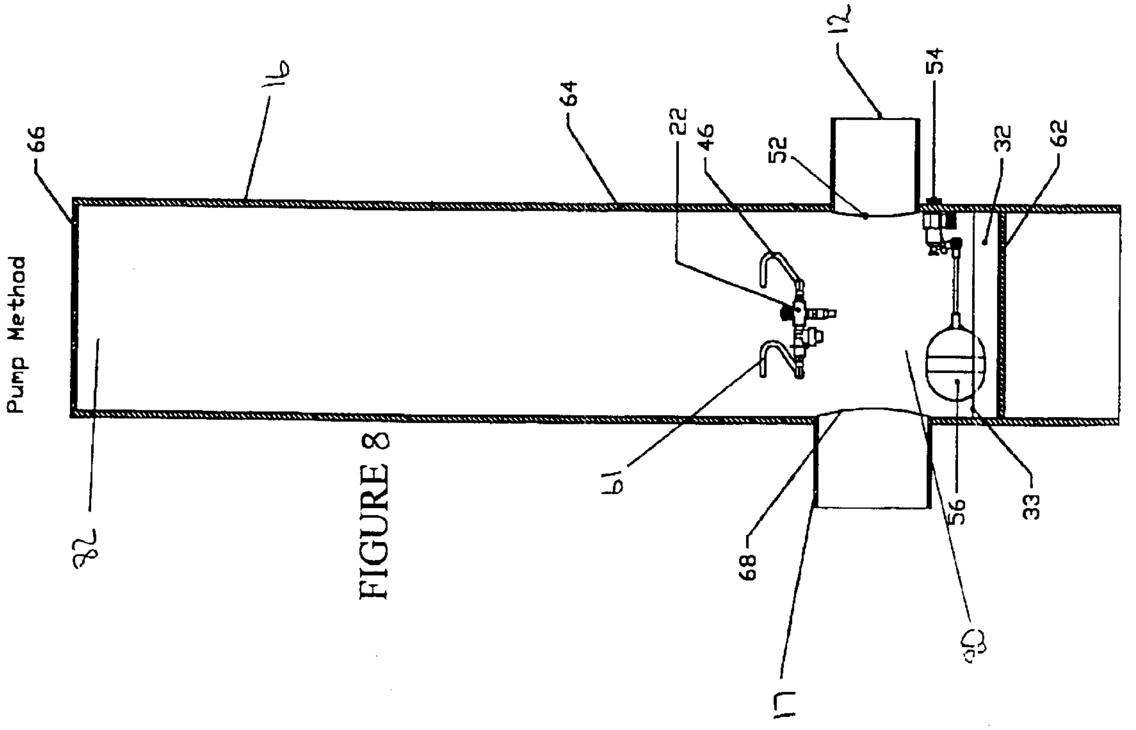
FIG. 8 shows a sectional side view of the vertical vaporization chamber including a nozzle for connection to a metering pump for liquid deodorant transfer.
Figure 10:
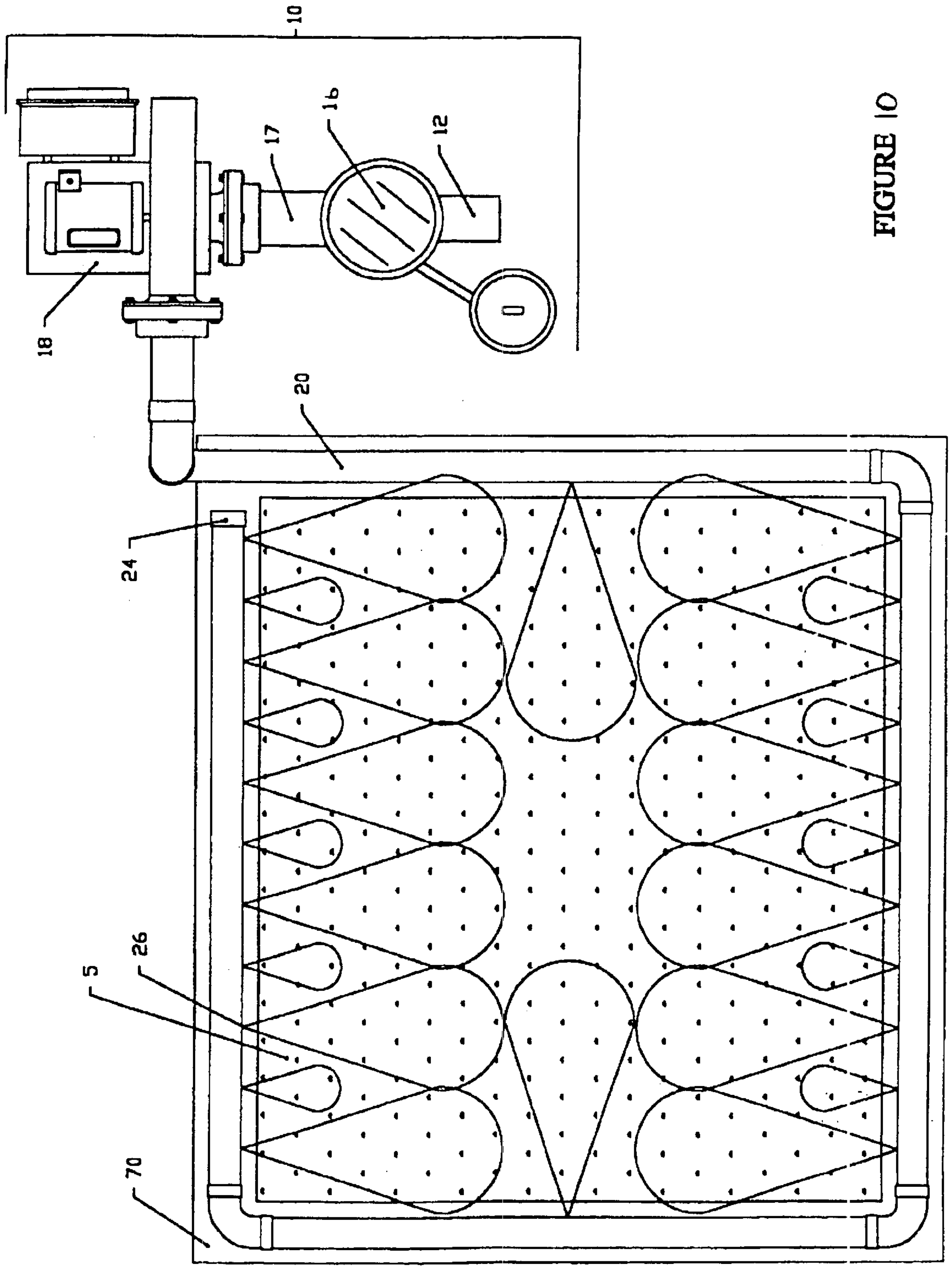
FIG. 10 shows a plan view of the liquid product vaporizing apparatus according to the present invention having a vertical vaporization chamber.

An alternative embodiment of the invention is shown in FIGS. 6–10. In this embodiment of the invention, the vaporization chamber is vertical, rather than horizontal. The vertical vaporization chamber can be particularly useful if the system must be installed in a small area where a horizontal vaporization chamber will not fit. Referring to FIGS. 7–9, the vaporization chamber 16 includes a chamber floor 62 and a chamber ceiling 66 with a cylindrical sidewall 64 defined between the chamber floor and the chamber ceiling. The air intake port 12 is connected directly to the vaporization chamber sidewall 64 near the chamber floor 62 to form the vaporization chamber inlet. 52. Diametrically opposed to the chamber inlet 52 is the chamber outlet 68, or outlet port, which connects to the air duct 17.

As shown in FIGS. 8–9, no treatment chamber is required in this embodiment of the invention because the liquid deodorant reservoir 32 and nozzle 22 are both held within the vaporization chamber 16. The liquid deodorant reservoir 32 is formed by the chamber floor 62 and sidewall 64, such that the upper liquid surface line 33 never reaches the chamber inlet 52 or chamber outlet 68. As with the previously described embodiment, a product maintenance device 54 keeps the deodorant level substantially constant at the upper liquid surface line 33. The product maintenance device is controlled by a float 56 and electric switch system which automatically operates an electric supply line valve to maintain the liquid in the reservoir at a desired level. A drain spigot 42 and supply tube 48 entrance is also provided in the sidewall 64 of vaporization chamber 16.

While the liquid deodorant reservoir 32 rests slightly below the chamber inlet 52 and chamber outlet 68, the nozzle 22 is held slightly above the chamber inlet 52 and chamber outlet 68 by a bracket (not shown). The nozzle 22 is directed with its tip 23 pointed upward toward the chamber ceiling 66. The nozzle 22 is hooked to an air supply line 46 which extends through sidewall 64 and provides pressurized air to the nozzle. If a metering pump is being used to deliver liquid deodorizer from the product reservoir to the nozzle, the nozzle will be connected to a pump tube 61 which extends through sidewall 64, as shown in FIG. 8. If a siphoning nozzle is being used to deliver liquid deodorizer from the product reservoir, a siphoning tube 60 will be connected to the nozzle, as shown in FIG. 9. A door 72 is provided on the vertical vaporization chamber 16 to provide easy access to the nozzle 22.

The vertical vaporization chamber is characterized by an air-flow end 80 and a closed end 82. The air-flow end 80 of the vaporization chamber includes the chamber inlet 52, the chamber outlet 68, and the product reservoir 32, all positioned beneath the nozzle 22. The air flowing into the vaporization chamber at the chamber inlet 52 generally flows directly across the chamber and out the chamber outlet 68. Accordingly, the air stream that flows within the system does not flow lengthwise through the vaporization chamber, but diametrically across the width of the vaporization chamber 16.

The closed end 82 of the vaporization chamber is simply an enclosed volume above the nozzle 22 which receives atomized particles of liquid deodorant from the nozzle. The closed end 82 of the vaporization chamber provides a space for rapid liquid deodorant vaporization apart from the main air stream of the system. Accordingly, non-vaporized liquid deodorant does not need to be inserted directly into the system air stream. A large portion of atomized particles sprayed from the nozzle 22 vaporize in the closed end 82 of the vaporization chamber. This vapor is then drawn through the chamber outlet 68 and into the air stream as the air stream flows through the vaporization chamber 16. Particles that do not vaporize tend to condense on the sidewall of the vaporization chamber. These liquid deodorant particles flow by gravity toward the air flow end 80 of the vaporization chamber and return to the liquid deodorant reservoir 32.

The operation of the alternative embodiment with a vertical vaporization chamber is similar to that of the previously described embodiment. Air is drawn into the system through the air intake port 12 by pressure blower 18. The air drawn into the air intake port 12 creates an air stream within the vapor distribution system 10. The air stream is passed through the air filter 28 to remove particulate matter from the air stream that could be damaging to the system. Next, the air stream enters the vaporization chamber 14 and passes under the nozzle.22. The air flowing through the vaporization chamber draws vaporized liquid deodorant from the closed end 82 of the vaporization chamber. The vaporized liquid deodorant mixes with the air stream to create a treated air stream flowing out of the vaporization chamber 16.

Treated air flows up through the vaporization chamber outlet 52 and is routed by air ducts 17 to the pressure blower 18. The treated air is drawn to the fan of the pressure blower 18, passes through the fan of the pressure blower, and is then forcibly pushed through the distribution pipes 20 and out the vapor release ports 26 to condition an odor source 5. As shown in FIG. 5, the odor source 5 might be an open tank, such as sewage treatment plant tank, and the distribution pipes 20 may be deployed along and around the perimeter of the open tank 70 to generate an air curtain of vaporized deodorant around the odor source 5.

Figure 14:
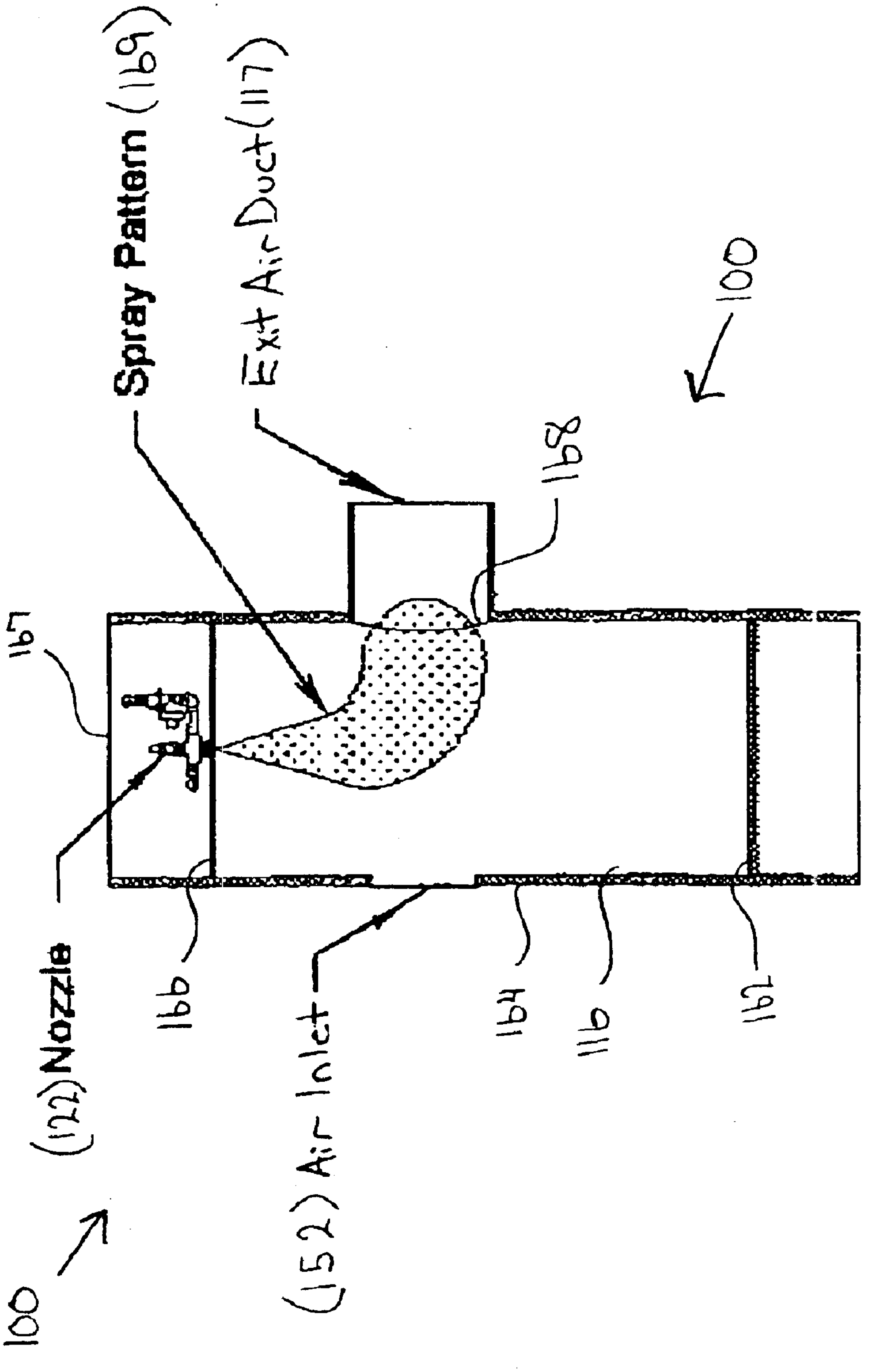
FIG. 14 shows an alternative embodiment of the liquid product vaporizing apparatus using the shear method.

Another alternative embodiment of the vapor distribution system of the present invention is shown in FIG. 14. The embodiment shown in FIG. 14 is called the "shear method" system and is similar to the embodiment shown in FIGS. 6–10, with variations as described below. According to the embodiment shown in FIG. 14, the vapor distribution system 100 includes a vaporization chamber 116 having a chamber floor 162 and a chamber ceiling 166 with a cylindrical sidewall 164 defined between the chamber wall and the chamber ceiling. The vaporization chamber inlet 152 is located on the middle portion of the vaporization chamber sidewall 164. Diametrically opposed to the chamber inlet is the chamber outlet 168, which connects to an exit air duct 117.

Similar to the embodiment shown in FIGS. 6–10, the shear method does not require a treatment chamber, because the nozzle 122 is held within the vaporization chamber 116. The nozzle 122 is held within the chamber ceiling 166 and, unlike the embodiment shown in FIGS. 6–10, the nozzle is directed with its tip pointed downward toward the chamber floor 162. The nozzle 122 is hooked to an air supply line (not shown) which enters the vaporization chamber through the chamber top 167 and provides pressurized air to the nozzle 122. A liquid product tube (not shown) is also connected to the nozzle 122 for providing liquid deodorizer from a product reservoir (not shown) to the nozzle. The product reservoir may be positioned above the vaporization chamber 116 or situated to the side of the vaporization chamber. Because of the arrangement of the vaporization chamber using the "shear method," a much smaller vaporization chamber may be used.

A blower (not shown) causes fresh, unsaturated air to be drawn into the vaporization chamber 116 through the air inlet 152. The air drawn into the chamber 116 through inlet 152 travels through the chamber and exits through the chamber outlet 168, where it is delivered to the air duct 117 and eventually to vapor release ports (not shown). The passage of air from the chamber inlet 152 to the chamber outlet 168 creates an air stream within the chamber 116 flowing from the air inlet 152 to the chamber outlet 168. The nozzle 122 sprays liquid deodorizer from the chamber ceiling 166 toward the chamber floor 162. When the liquid deodorizer spray 169 crosses the air stream, it is sheared by the air stream and directed through the chamber outlet 168 and into the air duct 117 along with the air stream. Because of this shearing effect of the air stream, the embodiment shown in FIG. 14 is known as the "shear method."

If the air stream flowing through the vaporization chamber 116 does not have the capacity to hold all of the atomized liquid deodorizer sprayed from the nozzle 122, some condensation will occur, and a small amount of liquid deodorizer will collect on the chamber floor 162. Liquid deodorizer that accumulates on the chamber floor 162 will naturally evaporate into the air above the chamber floor. This air containing evaporated liquid deodorizer is also drawn out of the chamber outlet 168 and into the air duct 117 as the air stream flows through the chamber 116. Fresh air from the air stream continually drifts into the chamber 116 to fill the chamber and replace any air exiting the chamber 116.

While the shear method provides for a much smaller vaporization chamber, it does not provide any solution for increasing the ability of the air stream to vaporize liquid deodorizer so that increased liquid deodorizer may be held by the air stream. Thus, the shear method is designed for those applications where condensation is not likely to occur. In other words, the shear method is designed for applications where only small amounts of liquid deodorizer need to be consumed and the temperature and humidity of the air stream are relatively consistent. Consumption of liquid deodorizer using the shear method is typically between 0.05 and 0.20 gallons per hour when the temperature of the air stream does not fall below 60 degrees Fahrenheit.

All of the above-described embodiments may be used on a wide variety applications. For example, the odor source 5 shown in FIGS. 5 and 10 might also be a garbage dump, in which case one or more distribution pipes are placed around or across the top of the dump to neutralize or mask the dump odor. Alternatively, the malodorous source might be the odor-producing structures of a waste treatment plant having digester and clarifier tanks. Other applications for the present invention include, but are not limited to, energy producing facilities, composting facilities, water treatment plants, asphalt plants, steel foundries, lift station scrubbers, pig farms or any other odor producing facilities, including positive collection or internal treatment systems having chemical scrubbers.

While the invention has been described, disclosed, illustrated and shown in certain preferred embodiments or modifications which it has assumed in practice, the scope of the invention is not intended to be, nor should it be deemed to be, limited thereby. For example, the described invention could be modified to cause the blower to push air through the vaporization chamber rather than draw air through the vaporization chamber. In some applications, the blower may not even be required because the vapors may be drawn from the vapor chamber under a vacuum produced by on-location air handling fans. In these applications, piping is used to connect the outlet of the vaporization chamber to the inlet side of an exhaust system, thereby creating a negative pressure at the outlet of the vaporization chamber and drawing air through the system. Other embodiments may completely remove the air pump which provides pressurized air to the nozzle because pressurized air is available from an alternative source. Still more embodiments may include a system wherein malodorous air, such as an industrial exhaust stream, is drawn into the system through the air inlet port, and the malodorous air is mixed with the vaporized liquid deodorant within the system rather than distributing the vaporized liquid deodorant to the malodor outside of the system. In other embodiments, the atomizing nozzle may be positioned on a floating platform within the vaporizing chamber in order to maintain a constant distance between the nozzle and the level of liquid deodorant within the product reservoir portion of the vaporizing chamber. This arrangement is helpful when the vapor chamber is located inside a sewer lift station that is filled manually with product on a periodic basis. Other modifications are possible and the scope of the present invention is not intended to be, nor should be, limited by the embodiment described herein.

What is claimed is:

1. A vapor delivery system for neutralizing malodors in a malodorous area, the vapor delivery system comprising:

a. a vaporization chamber having a sidewall positioned between a chamber ceiling and a chamber floor, the sidewall including an intake port positioned on the sidewall substantially diametrically opposed to an outlet port also positioned on the sidewall, the intake port and outlet port allowing the stream of air to enter said vaporization chamber through said intake port and exit said vaporization chamber through said outlet port, said vaporization chamber otherwise being enclosed with no obstructions positioned between the intake port and the outlet port;

b. at least one nozzle having a spray tip directed toward said chamber floor, said at least one nozzle receiving a stream of liquid to allow said nozzle to deliver an atomized spray of liquid into said vaporization chamber, said atomized liquid being vaporized in the vaporization chamber and incorporated in said stream of air to create a stream of treated air; and c. a distribution system communicating with said outlet port for delivering said stream of treated air to the malodorous area, said distribution system having at least one vapor release port for releasing said treated air stream to the malodorous area.

2. The vapor delivery system of claim 1 wherein said air intake port communicates with an air filter for removing air bound particles from said air stream before entering said vaporization chamber.

3. The vapor delivery system of claim 1 wherein said spray tip of said nozzle is positioned in said chamber ceiling.

4. The vapor delivery system of claim 1 further comprising a blower connected between said chamber outlet port and said distribution system, said blower operable to draw said stream of air into said air intake port and push said stream of treated air through said distribution system.

5. The vapor delivery system of claim 1 wherein the spray tip is arranged and disposed to deliver the atomized spray of liquid in a direction substantially perpendicular to the stream of air traveling between the inlet port and the outlet port in the vaporization chamber.

6. The vapor delivery system of claim 5 wherein the spray tip is arranged and disposed above the inlet port and the outlet port in the vaporization chamber.

7. A method of neutralizing malodors comprising the steps of:

a. providing an enclosed vaporization chamber having a chamber wall positioned between a chamber ceiling and a chamber floor, the chamber wall having an intake port and a diametrically opposed outlet port having no obstructions positioned therebetween for effecting circulation of air within the enclosed vaporization chamber;

b. drawing a stream of ambient air not received from an exhaust stream through said intake port and into said vaporization chamber such that the stream of ambient air travels through the vaporization chamber from the intake port to the diametrically opposed outlet port;

c. spraying an atomized liquid deodorant into said vaporization chamber through a nozzle having a spray tip;

d. bringing said stream of ambient air into contact with said atomized liquid deodorant in said vaporization chamber so that said liquid vaporizes into said stream of ambient air to create a stream of treated air leaving the vaporization chamber; and e. delivering said stream of treated air through said outlet port to a distribution system having at least one vapor release port for releasing said stream of treated air from said distribution system.

8. The method of claim 7 wherein the spray tip of the nozzle sprays liquid deodorant toward said chamber floor.

9. The method of claim 8 wherein the spray tip of the nozzle is positioned above the intake port and the outlet port in the vaporization chamber.

10. The method of claim 9 wherein the spray tip of the nozzle sprays liquid deodorant from the nozzle in a direction substantially perpendicular to the stream of ambient air traveling through vaporization chamber from the intake port to the diametrically opposed outlet port.

11. The method of claim 7 wherein the spray tip of the nozzle sprays liquid deodorant toward said chamber ceiling.

12. The method of claim 11 wherein the spray tip of the nozzle is positioned above the intake port and the outlet port in the vaporization chamber.

13. The method of claim 12 wherein the spray tip of the nozzle sprays liquid deodorant from the nozzle in a direction substantially perpendicular to the stream of ambient air traveling through vaporization chamber from the intake port to the diametrically opposed outlet port.

14. A vapor delivery system for neutralizing malodors in a malodorous area, the vapor delivery system comprising:

a. a vaporization chamber for vaporizing a liquid in a stream of ambient air before delivery of the liquid to the malodorous area located outside of the vaporization chamber, the vaporization chamber having a sidewall positioned between a chamber ceiling and a chamber floor, the sidewall including an intake port positioned on the sidewall substantially diametrically opposed to an outlet port also positioned on the sidewall, the intake port positioned to receive the stream of ambient air not received from an exhaust stream, the intake port and outlet port having no obstructions therebetween for effecting the circulation of the stream of ambient air within the vaporization chamber, thereby allowing the stream of air to enter said vaporization chamber through said intake port and exit said vaporization chamber through said outlet port, said vaporization chamber otherwise being enclosed;

b. at least one nozzle having a spray tip directed toward said chamber ceiling, said at least one nozzle receiving a stream of liquid to allow said nozzle to deliver an atomized spray of liquid into said vaporization chamber, said atomized liquid being vaporized in the vaporization chamber and incorporated in said stream of air to create a stream of treated air; and c. a distribution system communicating with said outlet port for delivering said stream of treated air to the malodorous area, said distribution system having at least one vapor release port for releasing said treated air stream to the malodorous area.

15. The vapor delivery system of claim 14 wherein said air intake port communicates with an air filter for removing air bound particles from said air stream before entering said vaporization chamber.

16. The vapor delivery system of claim 14 further comprising a blower connected between said chamber outlet port and said distribution system, said blower operable to draw said stream of air into said air intake port and push said stream of treated air through said distribution system.

17. The vapor delivery system of claim 14 wherein the spray tip is arranged and disposed to deliver the atomized spray of liquid in a direction substantially perpendicular to the stream of air traveling between the inlet port and the outlet port in the vaporization chamber.

18. The vapor delivery system of claim 17 wherein the spray tip is arranged and disposed above the inlet port and the outlet port in the vaporization chamber.

* * * * *